United States Patent [19]

Laurent et al.

[11] 4,008,313
[45] Feb. 15, 1977

[54] NOVEL CORTICOIDS

[75] Inventors: Henry Laurent; Rudolf Wiechert; Peter Klaus Mengel, all of Berlin; Karl-Heinz Kolb, Hamburg, all of Germany

[73] Assignee: Schering Aktiengesellschaft, Berlin & Bergkamen, Germany

[22] Filed: Oct. 7, 1975

[21] Appl. No.: 620,411

[30] Foreign Application Priority Data
Oct. 9, 1974 Germany .......................... 2448662

[52] U.S. Cl. .............................. 424/242; 424/243; 260/397.45
[51] Int. Cl.² ........................................ A61K 31/56
[58] Field of Search ............. 260/397.45; 424/242, 424/243

[56] References Cited
UNITED STATES PATENTS 3,828,083  8/1974  Kieslich et al. ............... 260/397.45
3,845,085  10/1974  Phillipps et al. ............... 260/397.45

Primary Examiner—Elbert L. Roberts
Attorney, Agent, or Firm—Millen & White

[57] ABSTRACT

Corticoids of the formula

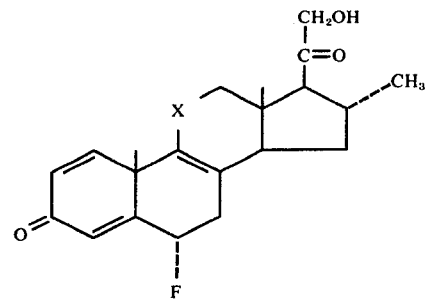

wherein X is β-hydroxymethylene or carbonyl, and 21-esters thereof with physiologically acceptable acids possess topical anti-inflammatory activity with relatively little systemic activity.

13 Claims, No Drawings

NOVEL CORTICOIDS

BACKGROUND OF THE INVENTION

This invention relates to novel, pharmacologically active corticoids, to a process for the preparation thereof and to pharmaceutical compositions containing them.

SUMMARY OF THE INVENTION

In a composition aspect, this invention relates to novel corticoids to the general Formula I

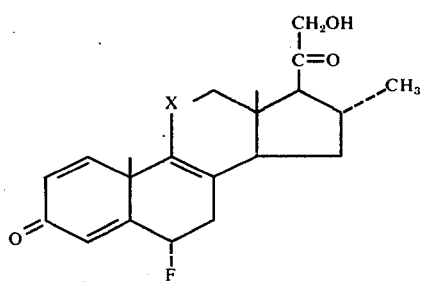

wherein X is β-hydroxymethylene or carbonyl, and 21-esters thereof with physiologically acceptable acids.

In another composition aspect, this invention relates to pharmaceutical compositions comprising a compound of this invention in admixture with a pharmaceutically acceptable carrier.

In process aspects, this invention relates to processes for the production and use of the compounds of this invention.

DETAILED DISCUSSION

The preferred 21-esters of the 21-hydroxy compounds of Formula I are esters of alkanoic acids 1-12, (more preferably 2-8), carbon atoms, e.g., esters whose acyl group is formyl, acetyl, propionyl, butyryl, pentanoyl, hexanoyl, octanoyl, undecanoyl, dimethylacetyl, trimethylacetyl, diethylacetyl or tert.-butylacetyl. However, because activity resides in the unesterified corticoid, contemplated equivalents of the preferred esters of alkanoic acids of 1-12 carbon atoms are 21-esters of all physiologically acceptable acids, including carboxylic acids of 1-16 carbon atoms and sulfonic, sulfuric and phosphoric acids, including straight-chain or branched, saturated or unsaturated aliphatic mono- or dicarboxylic acids, which can be unsubstituted or substituted in the usual way, for example, by hydroxy, amino, or by halogen atoms, including cycloaliphatic, aromatic, mixed aromatic-aliphatic, and heterocyclic carboxylic and sulfonic acids, including those whose acyl group is aroyl, e.g., aralkanoyl, e.g., phenacetyl, cyeloalkanoyl and cycloalkylalkanoyl, e.g., cyclopentylpropionyl, and the corresponding substituted acyl, e.g., hydroxyacetyl, monochloroacetyl, dichloroacetyl, trichloroacetyl, dimethylaminoacetyl, trimethylaminoacetyl, diethylaminoacetyl, piperidinoacetyl, nicotinoyl, ω-carboxypropionyl, and ω-carboxypentanoyl.

To prepare water-soluble derivatives of the 21-hydroxy compounds, esters can be formed whose acyl group contains a basic nitrogen group, which can be converted into a pharmaceutically acceptable acid addition salts thereof, such as, for example, the hydrochloride, hydrobromide, sulfate, phosphate, oxalate, tartrate, or maleate salt.

Alternatively, the 21-mono-esters of dicarboxylic acids, of sulfuric acid, and of phosphoric acid can be converted into salts thereof with bases, e.g., the sodium or potassium salts, or into the ammonium salts, to increase their water solubility.

In a process aspect, this invention relates to the production of the novel corticoids by splitting off hydrogen bromide in a conventional manner from a compound of general Formula II

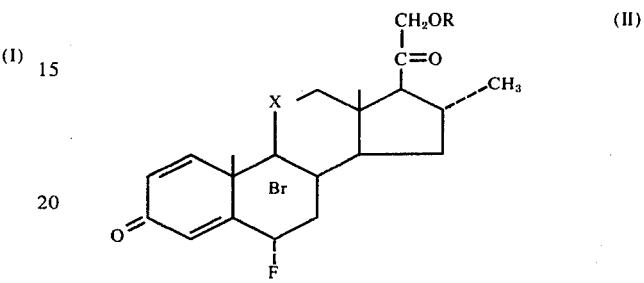

wherein X and R is a hydrogen atom or acyl, as defined hereinabove, preferably alkanoyl, and optionally thereafter the 21-ester group of the thus-produced compound of this invention is saponified, or the free 21-hydroxy group thereof is esterified and/or the 11-hydroxy group thereof is oxidized to a keto group. The starting 9α-bromo steroids are known (U.S. Pat. No. 3,232,839).

The splitting off of hydrogen bromide from the compounds of general Formula II can be conducted under conditions conventionally employed in the steroid chemistry for splitting off hydrogen bromide from bromohydrins or α-bromo-ketones.

Thus, the step of splitting off hydrogen bromide can be accomplished, for example, by heating the compounds of general Formula II under reflux in a tertiary amine, such as pyridine, lutidine or preferably collidine.

Another suitable method is the reaction of compounds of general Formula II with a lithium salt and/or calcium carbonate in dimethylformamide or dimethylacetamide.

The optional step of oxidizing the 11β-hydroxy steriods of general Formula I to the corresponding 11-ketones is effected according to conventional operating methods, for example with chromic acid, N-bromosuccinimide, or N-bromoacetamide.

The optional saponification of the 21-esters can be conducted according to known processes, for example, saponification in water or an aqueous alcohol in the presence of an acidic catalyst, such as hydrochloric acid, sulfuric acid, p-toluenesulfonic acid, or in the presence of an alkaline catalyst, such as potassium bicarbonate, potassium carbonate, sodium hydroxide, or potassium hydroxide.

The optional esterification of the free hydroxy group in the 21-position likewise can be conducted according to conventional methods, with an acyl chloride or acyl anhydride in the presence of an acid, e.g., hydrogen chloride, p-toluenesulfonic acid, trifluoroacetic acid, or in the presence of a base, such as potassium carbonate, pyridine, collidine, or p-dimethylaminopyridine.

It is also possible to esterify with carboxylic acids in the presence of trifluoroacetic acid anhydride.

The alkali salts of the 21-monosulfuric acid esters of the 21-hydroxy compounds of general Formula I can be prepared in a conventional manner, for example, by reacting the 21-hydroxy compounds with sulfur trioxide in pyridine and converting the thus-obtained sulfuric acid ester into an alkali salt thereof by treatment with an alkali base.

The alkali salts of the 21-monophosphoric acid esters can be prepared in a conventional manner from the 21-hydroxy compounds of general Formula I, for example by esterifying the 21-hydroxy compounds with sulfonic acid chloride in the 21-position, converting the 21-sulfonates with alkali iodide in acetone into the 21-iodine compounds, reacting the latter with phosphoric acid in the presence of an organic base, and converting the thus-obtained phosphoric acid monoesters with alkali into their dialkali metal salts.

The novel 21-hydroxy corticoids of general Formula I and their 21-esters with pharmaceutically acceptable acids are pharmacologically active and distinguished in particular by a pronounced topical anti-inflammatory activity. Moreover, they possess substantially lower corticoid activity upon systemic administration than the corticoids of an analogous structure saturated in the 8-position.

Their activity is often distinguished by a rapid onset of activity, a high intensity and long duration of effectiveness. They possess a favorable resorbability and have a relatively good stability in galenic preparations.

The novel compounds are useful, in admixture with pharmaceutically acceptable carriers conventional in galenic pharmacy, for the topical treatment of contact dermatitis, eczema of a great variety of types, neurodermatoses, erythrodermia, burns, pruritus valvae et ani, rosacea, erythematodes cutaneus, psoriasis, lichen ruber planus et verrucosus, and similar skin diseases.

Such pharmaceutical compositions can be produced in the usual way by incorporating the active agents, together with suitable additives, into the desired form of application, e.g., solutions, lotions, ointments, creams and plasters. In the thus-formulated medicinal agents, the concentration of the active compound is dependent on the mode of administration. For example, in lotions and ointments, concentration of 0.001 to 1% is preferred.

The novel compounds can also be employed in inhalants, optionally in combination with the usual vehicles and auxiliary agents.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

15.0 g. of 6α-fluoro-9α-bromo-11β-hydroxy-21-hexanoyloxy-16α-methyl-1,4-pregnadiene-3,20-dione is dissolved in 25 ml. of collidine and agitated for 15 minutes at 170° C. After cooling, the collidine hydrobromide is filtered off and the filtrate combined with ether until no precipitate is formed any longer. The precipitate is filtered off, and the filtrate is extracted with hydrochloric acid and sodium bicarbonate; then, it is washed neutral, dried, and concentrated. The viscous crude product amounting to 17.7 g. is purified by chromatography over a silica gel column, and recrystallization from acetone-hexane yields 6α-fluoro-11β-hydroxy-21-hexanoyloxy-16α-methyl-1,4,8-pregnatriene-3,20-dione, m.p. 155° C.

EXAMPLE 2

3.85 g. of 6α-fluoro-11β-hydroxy-21hexanoyloxy-16α-methyl-1,4,8-pregnatriene-3,20-dione is dissolved in 38.5 ml. of methylene chloride. The solution is combined with 58 ml. of methanolic potassium hydroxide solution and stirred under nitrogen for 15 minutes at room temperature.

Thereafter, the reaction solution is mixed with water until two clear strata are formed. The methylene chloride is used for extraction. The methylene chloride phases are combined, washed neutral, dried, and concentrated. The crude product of 3.09 g. is purified by chromatography, and recrystallization from acetone-hexane yields 6α-fluoro-11β,21-dihydroxy-16α-methyl-1,4,8-pregnatriene-3,20-dione, m.p. 173° C.

EXAMPLE 3

1.6 g. of 6α-fluoro-11β,21-dihydroxy-16α-methyl-1,4,8-pregnatriene-3,20-dione is dissolved in 8 ml. of pyridine. The solution is combined with 4 ml. of acetic anhydride and stirred for 1 hour at room temperature. Thereafter, the reaction solution is introduced into water and agitated for 30 minutes. The thus-obtained precipitate is filtered off and dissolved in methylene chloride. The solution is washed neutral, dried, and concentrated. The crude product of 1.5 g. is purified by chromatography and recrystallized from acetone-hexane, thus obtaining 6α-fluoro-11β-hydroxy-21-acetoxy-16α-methyl-1,4,8-pregnatriene-3,20-dione, m.p. 176° C.

EXAMPLE 4

2.15 g. of 6α-fluoro-11β,21-dihydroxy-16α-methyl-1,4,8-pregnatriene-3,20-dione is dissolved in 4.3 ml. of pyridine. The solution is combined with 2.15 ml. of butyric acid anhydride and stirred at room temperature. After 1 hour, the reaction solution is introduced into ice water; the thus-formed precipitate is filitered off and dissolved in methylene chloride. The methylene chloride solution is washed neutral, dried, and concentrated. The crude product of 2.6 g. is purified by chromatography, and recrystallization from methylene chloride-diisopropyl ether yields 6α-fluoro-11β-hydroxy-21-butyryloxy-16α-methyl-1,4,8-pregnatriene-3,20-dione, m.p. 112° C.

EXAMPLE 5

2.15 g. of 6α-fluoro-11β,21-dihydroxy-16α-methyl-1,4,8-pregnatriene-3,20-dione is dissolved in 4.3 ml. of pyridine. The solution is combined with 2.15 ml. of valeric acid anhydride and agitated at room temperature. After one hour, the reaction solution is introduced into ice water; the thus-formed precipitate is filtered off and dissolved in methylene chloride. The solution is washed neutral, dried, and concentrated. The crude product is purified by chromatography and recrystallized from methylene chloride-diisopropyl ether, thus obtaining 6α-fluoro-11β-hydroxy-21-valeryloxy-16β-methyl-1,4,8-pregnatriene-3,20-dione, m.p. 151° C.

EXAMPLE 6

300 mg. of 6α-fluoro-11β-hydroxy-21-hexanoyloxy-16α-methyl-1,4,8-pregnatriene-3,20-dione is dissolved in 7.5 ml. of acetone, combined with 0.36 ml. of a chromium (VI) oxide solution, and stirred for 1 hour at room temperature. The reaction solution is stirred into ice water; the thus-formed precipitate is vacuum-filtered and dissolved in methylene chloride. The methylene chloride solution is washed neutral, dried, and evaporated under vacuum. The crude product is purified by chromatography, and recrystallization from hexane-acetone yields 6α-fluoro-21-hexanoyloxy-16α-methyl-1,4,8-pregnatriene-3,11,20-trione, m.p. 159° C.

Following the procedure of Example 2, 6α-fluoro-16α-methyl-1,4,8-pregnatriene-3,11,20-dione is produced by the hydrolysis of the above thus-produced 21-hexanoyloxy ester thereof.

EXAMPLE 7

Under the conditions described in Example 6, 500 mg. of 6α-fluoro-11β-hydroxy-21-valeryloxy-16α-methyl-1,4,8-pregnatriene-3,20-dione is oxidized with a chromium (VI) oxide solution. The crude product is purified by chromatography and recrystallized from acetone-hexane, thus obtaining 6α-fluoro-21-valeryloxy-16α-methyl-1,4,8-pregnatriene-3,11,20-trione, m.p. 161° C.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A corticoid of the formula

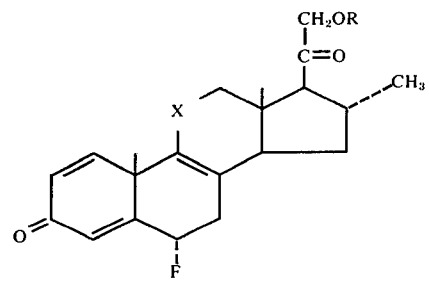

wherein X is β-hydroxymethylene or carbonyl, and R is a hydrogen atom or alkanoyl of 1 to 12 carbon atoms.

2. A compound of claim 1 wherein X is β-hydroxymethylene.

3. A compound of claim 1 wherein X is carbonyl.

4. A compound of claim 1 wherein R is alkanoyl of 2–8 carbon atoms.

5. 6α-Fluoro-11β-hydroxy-21-hexanoyloxy-16αmethyl-1,4,8-pregnatriene-3,20-dione, a compound of claim 1.

6. 6α-Fluoro-11β,21-dihydroxy-16α-methyl-1,4,8-pregnatriene-3,20-dione, a compound of claim 1.

7. 6α-Fluoro11β-hydroxy-21-acetoxy-16α-methyl-1,4,8-pregnatriene-3,20-dione, a compound of claim 1.

8. 6α-Fluoro-11β-hydroxy-21-butyryloxy-16α-methyl-1,4,8-pregnatriene-3,20-dione, a compound of claim 1.

9. 6α-Fluoro-11β-hydroxy-21-valeryloxy-16α-methyl-1,4,8-pregnatriene-3,20-dione, a compound of claim 1.

10. 6α-Fluoro-21-hexanoyloxy-16α-methyl-1,4,8-pregnatriene-3,11,20-trione, a compound of claim 1.

11. 6α-Fluoro-21-valeryloxy-16αmethyl-1,4,8-pregnatriene-3,11,20-trione, a compound of claim 1.

12. A pharmaceutical composition comprising a compound of claim 1 in admixture with a pharmaceutically acceptable carrier.

13. A method for the treatment of inflammations of the skin which comprises topically administering to the affected skin an anti-inflammatorily effective amount of a compound of claim 1.

* * * * *